United States Patent
Adair et al.

(10) Patent No.: US 8,530,039 B2
(45) Date of Patent: Sep. 10, 2013

(54) POLYCRYSTALLINE COMPLEX-SHAPED MESOSCALE COMPONENTS

(75) Inventors: James H. Adair, State College, PA (US); Mary Frecker, State College, PA (US); Christopher Muhlstein, University Park, PA (US); Eric Mockensturm, State College, PA (US); Harriet Black Nembhard, University Park, PA (US); Randy S. Haluck, Lititz, PA (US); Abraham Mathew, Hershey, PA (US); Nicholas Antolino, University Park, PA (US); Gregory R Hayes, State College, PA (US); Milton Aguirre, State College, PA (US); Rebecca Kirkpatrick, University Park, PA (US); Chumpol Yuangyai, University Park, PA (US)

(73) Assignee: The Penn State Research Foundation, University Park, PA (US)

( * ) Notice: Subject to any disclaimer, the term of this patent is extended or adjusted under 35 U.S.C. 154(b) by 898 days.

(21) Appl. No.: 12/534,329

(22) Filed: Aug. 3, 2009

(65) Prior Publication Data

US 2010/0075170 A1 Mar. 25, 2010

Related U.S. Application Data

(60) Provisional application No. 61/150,568, filed on Feb. 6, 2009, provisional application No. 61/085,506, filed on Aug. 1, 2008.

(51) Int. Cl.
*B32B 1/00* (2006.01)
*B32B 3/00* (2006.01)

(52) U.S. Cl.
USPC ............................................. 428/174

(58) Field of Classification Search
USPC ................... 428/174, 546; 600/564, 566
See application file for complete search history.

(56) References Cited

U.S. PATENT DOCUMENTS

| 4,007,732 A | 2/1977 | Kvavle et al. |
| 4,401,124 A | 8/1983 | Guess et al. |

(Continued)

FOREIGN PATENT DOCUMENTS

| CN | 1978385 | 6/2007 |
| EP | 0206055 | 12/1986 |
| JP | 2007038304 | 2/2007 |

OTHER PUBLICATIONS

Byun, S. et al., Barbed micro-spikes for micro-scale biopsy, *Journal of Micromechanics and Microengineering*, 15: 1279-84, 2005.

(Continued)

*Primary Examiner* — Catherine A Simone
(74) *Attorney, Agent, or Firm* — Gifford, Krass, Sprinkle, Anderson & Citlowski, P.C.; Douglas L. Wathen

(57) ABSTRACT

A polycrystalline mesoscale component, formed through a process including filing a mold cavity formed in a photoresist with a mold fill, is provided with an overall length L divided into multiple segments with a second segment extending from a first segment at a nonlinear angle. The first segment has a first segment height H1 and a first segment thickness T1, while the second segment has a second segment height H2 and a second segment thickness T2, with the lesser of H1 and H2 defining a minimum segment height Hmin and the lesser of T1 and T2 defining a minimum segment thickness Tmin. The resultant component has a ratio of L:Hmin:Tmin of 20-80:1:0.5-10 where Hmin is between 5 and 500 microns. In specific instances, the nonlinear angle is acute, the multiple segments are rectilinear in cross section, and a segment thickness has an edge resolution of between 0.1 and 2 microns.

19 Claims, 5 Drawing Sheets

(56) References Cited

U.S. PATENT DOCUMENTS

| | | | |
|---|---|---|---|
| 4,674,271 | A | 6/1987 | Bird |
| 4,821,717 | A | 4/1989 | Wehrli |
| 4,958,625 | A | 9/1990 | Bates et al. |
| 5,660,186 | A | 8/1997 | Bachir |
| 6,242,163 | B1 | 6/2001 | Stampfl et al. |
| 2004/0165243 | A1* | 8/2004 | Helmbrecht ............... 359/223 |
| 2007/0026537 | A1 | 2/2007 | Jiang et al. |
| 2009/0299219 | A1 | 12/2009 | Pflueger |
| 2010/0076342 | A1 | 3/2010 | Miller |

OTHER PUBLICATIONS

Figueredo, S. et al., Design of an Endoscopic Biopsy Needle with Flexural Members, *Journal of Medical Devices*, 1: Mar. 1-8, 2007.

Islam, A., A New Single-Use Bone Marrow Biopsy Needle, *Biomedical Instrumentation & Technology*, 39(5): 391-96, Sep./Oct. 2005.

Niebel, C., Frecker, M., Mathew, A., Rau, A., Hayes, G., "Design of an Endoscopic Biopsy Needle," *Proceedings ASME Design of Medical Devices Conference*, Apr. 2010, Minneapolis, MN, Paper DMD2010-3836.

Janney, Mark A., Omatete, Ogberni O., Walls, Claudia A., Nunn, Stephen D., Ogle, Randy J., and Westmoreland, Gary, "Development of Lox-Toxicity Gelcasting Systems," J. Am. Ceram. Soc., 81(3) 581-591 (1998).

Aguirre, Milton E., Frecker, Mary, "Design Innovation Size and Shape Optimization of a 1.0 mm Multifunctional Forceps-Scissors Surgical Instrument", *J. Medical Devices*, vol. 2(1), Mar. 2008.

Antolino, Nicholas E., Hayes, Gregory, Kirkpatrick, rebecca, Muhlstein, Christopher L., Frecker, Mary I., Mockensturm, Eric M., Adair, James H., "Last Mold Rapid Infiltration Forming of Mesoscale Ceramics: Part 1, Fabrication", *J. Am. Ceram. Soc.*, 92(S1) S63-S69 (2009).

Antolino, Nicholas E., Hayes, Gregory, Kirkpatrick, Rebecca, Muhlstein, Christopher L., Frecker, Mary I., Mockensturm, Eric, M., Adair, James H., "Lost Mold-Rapid Infiltration Forming of Mesoscale Ceramics: Part 2, Geometry and Strength Improvements," *J. Am. Ceram. Soc.*, 92(S1) S70-S78 (2009).

Aguirre, M.E., Hayes, G., Frecker, M., Adair, J., Antolino, N., "Fabrication and Design of a Nanoparticulate Enabled Micro Forceps," Proceedings of the IDETC/CIE 2008 ASME 2008 International Design Engineering Technical Conferences & Computers and Information in Engineering Conference, Aug. 3-6, 2008, New York City, NY, Paper DETC2008-49917.

* cited by examiner

FIG. 4
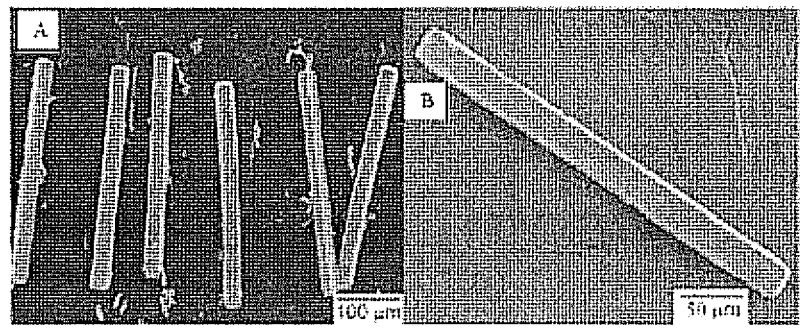
FIGS. 5(a) and (b)
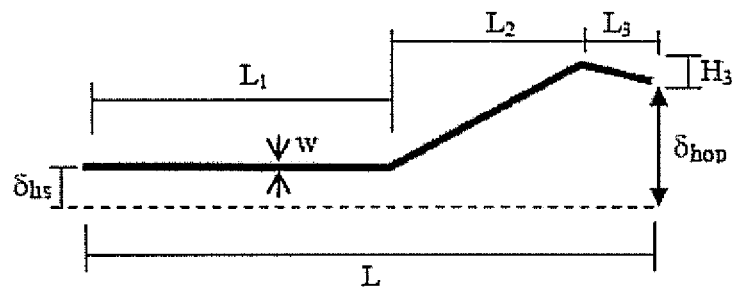
FIG. 7

POLYCRYSTALLINE COMPLEX-SHAPED MESOSCALE COMPONENTS

CROSS-REFERENCE TO RELATED APPLICATIONS

This application claims priority of U.S. Provisional Patent Applications Ser. No. 61/085,506 filed Aug. 1, 2008, and Ser. No. 61/150,568 filed Feb. 6, 2009, the contents of which are incorporated herein by reference.

GOVERNMENT INTEREST

The present invention is funded in part through National Institutes of Health Grant No. R21EB006488; National Science Foundation Grant No. IIP0637850 and funding through the National Science Foundation Cooperative Agreement No. 0335765. The United States government as a result may retain certain rights herein.

FIELD OF THE INVENTION

The present invention in general relates to the formation of mesoscale components from particulate and in particular to densified polycrystalline complex-shaped mesoscale components adhering to high tolerances.

BACKGROUND OF THE INVENTION

A variety of fields would benefit from the size reduction of mechanical structures. By way of example, minimally invasive surgery requires a full complement of surgical instruments capable of operation with a remote manipulator with the instruments operating within an endoscope. To satisfy these requirements for miniaturized devices, mesoscale components must be produced with complex shapes, from a variety of materials, and high manufacturing tolerances. Existing manufacturing techniques are inadequate as failing to satisfy one or more of these requirements. MEMS are capable of forming complex shapes, the etch techniques limit material choices to crystalline and amorphous silicon and inorganic silicon compounds such as silicon oxides. Additionally, MEMS etch and lithography techniques fail to maintain tolerances in high aspect ratio components and are not applicable in polycrystalline materials. Other conventional fabrication techniques such as CNC machining and precision wire EDM lack sufficient control to provide the complex shapes and small feature sizes and high tolerances that would be required. Additionally, other machining techniques capable of producing complex shapes such as chemical etching, focused ion beam etching or fast atom beam machining, while having many attributes that are attractive to production of such mesoscale components, only produce single components at a time and are limited as to the materials that can be so machined.

The inability to form polycrystalline complex shaped mesoscale components has limited advancements in a number of fields as the mechanical properties of the component cannot be controlled to the same degree in crystalline or amorphous materials. Owing to the forces such components would experience in a variety of environments such as surgery or subterranean sampling, a high degree of strength and resistance to catastrophic failure must be incorporated into such a mesoscale component.

Thus, there exists a need for a polycrystalline complex shaped mesoscale component and a process for producing the same. There further exists a need for such a component containing an inhomogeneous grain structure or reinforcing filler.

SUMMARY OF THE INVENTION

A polycrystalline mesoscale component is provided that has an overall length L divided into multiple segments with a second segment extending from a first segment at a nonlinear angle. The first segment has a first segment height $H_1$ and a first segment thickness $T_1$, while the second segment has a second segment height $H_2$ and a second segment thickness $T_2$, with the lesser of $H_1$ and $H_2$ defining a minimum segment height $H_{min}$ and the lesser of $T_1$ and $T_2$ defining a minimum segment thickness $T_{min}$. The resultant component has a ratio of $L:H_{min}:T_{min}$ of 20-80:1:0.5-10 where $H_{min}$ is between 5 and 500 microns. In specific instances, the nonlinear angle is acute, the multiple segments are rectilinear in cross section, and a segment thickness has an edge resolution of between 0.1 and 2 microns.

A process for forming a polycrystalline mesoscale component is provided that includes filling a mold cavity formed in a photoresist with a mold fill. The mold fill includes a slurry of particles of ceramic, metal, or a combination thereof in a polymerizable monomer in an amount to form a polymer that imparts strength to the mold fill. Thereafter the photoresist is removed and the gel cast mold fill is heated to remove the polymer and form the polycrystalline sintered mesoscale component. In a particular embodiment, the mold fill after removal of the photoresist is heated in contact with a second mold fill to form a composite component with a sintered interface between the mold fill and the second mold fill.

BRIEF DESCRIPTION OF THE DRAWINGS

FIG. 4 is a cross-sectional scanning electron micrograph (SEM) of the fabrication mold;

FIGS. 5A and 5B are SEMs of zirconia test bars (A) and a cleaned, magnified test bar (B) as shown in (A);

FIG. 7 is a plan view of an inventive component of FIG. 1A as a micro forceps part annotated to show additional geometric variables.

DETAILED DESCRIPTION OF THE PREFERRED EMBODIMENTS

The present invention has utility as a variety of mechanical component of mesoscale dimensions and is described with respect to an exemplary manipulator of surrounding material. An inventive component has geometries previously unattainable and formed from a variety of compositions. An inventive component is characterized by a ratio of component length L to minimum component segment height $H_{min}$ to component segment minimal thickness $T_{min}$ of L:$H_{min}$:$T_{min}$ of 20-80:1: 0.5-5 for components in which $H_{min}$ is between 5 and 500 microns and the component is characterized by discontinuous edges. The component is formed from a variety of materials including metals, ceramics, alloys, and reinforced forms thereof to produce polycrystalline components of dimensions and compositions previously unattainable.

As used herein, "discontinuous edges" is defined as a sharp edge having a polygonal cross section in at least a portion of the component. The discontinuous edges as produced in an inventive component have an edge resolution of between 0.1 and 2 microns with feature resolutions as fine as 0.2 microns and commonly produced with a resolution of 2 microns for a particular feature.

As used herein, "edge resolution" is defined as the radius of curvature at an edge. Edge resolution is typically limited by grain size of a polycrystalline inventive component.

Figure 1A:
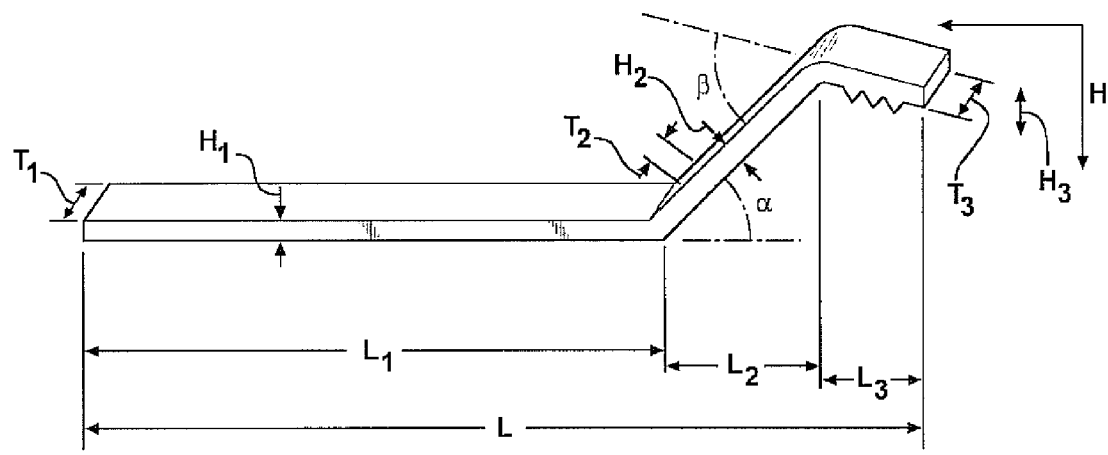
FIG. 1A is a perspective view of an inventive component.
Figure 1B:
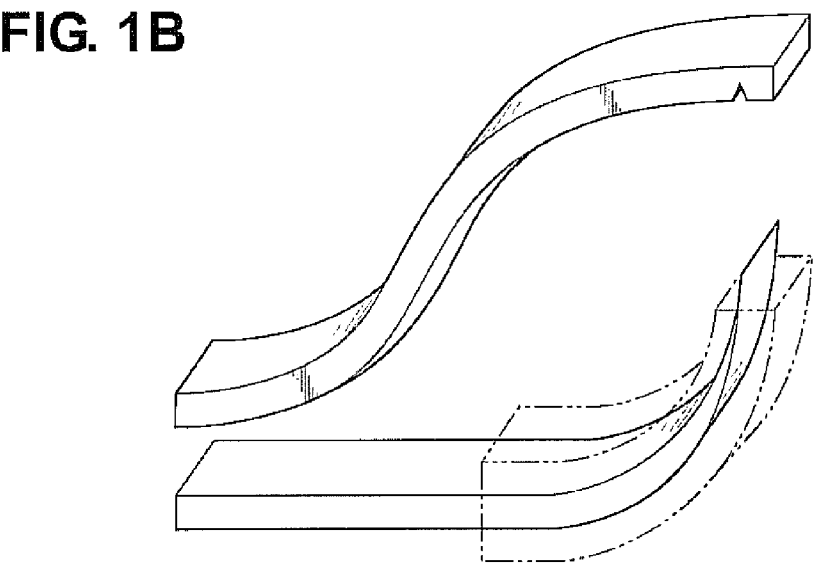
FIG. 1B is a perspective view of a pair representative inventive components forming an anvil and cutter pair, the cutter having a lap joint with a reinforcing portion.

FIG. 1A depicts an inventive component generally at 10 where L is the total length of the component and $L_1$, $L_2$ and $L_3$ are the respective lengths of segments 1, 2 and 3. Each of the segments of component 10 has a respective height $H_1$, $H_2$ and $H_3$ as well as a respective thickness $T_1$, $T_2$ and $T_3$. In contrast to prior art lithographic formation techniques that are well suited for forming structures from silicon or silicon oxide with L:$H_{min}$ values of less than 20:1 that disfavor nonorthogonal angles α and β per FIG. 1A and edge resolutions that are poor, components according to the present invention are readily formed in reproducible batches from a variety of nanoparticulate precursors with improved attributes relative to lithographic formation techniques. An inventive component is also characterized by different dimensions in the component segments per FIG. 1A. This difference in segment dimensions is manifest in that component area in a plane of length L and height H, $A_{LH}$ is optionally less than 40% of LH as a rectilinear area. A component area $A_{LH}$ is readily formed with an area of 10 to 30% of LH with the lower end of this range corresponding to a component of higher curvature and comparative lesser height relative to the higher end of this range of component areas. FIG. 1B is a perspective view of an anvil component and a complementary cutter component according to the present invention. The cutter component has a lap joint between an arcuate cutting portion and a reinforcing portion sintered thereto. The anvil component and the cutting portion both have the dimensionality of an inventive component.

Manufacturing

Figure 2:
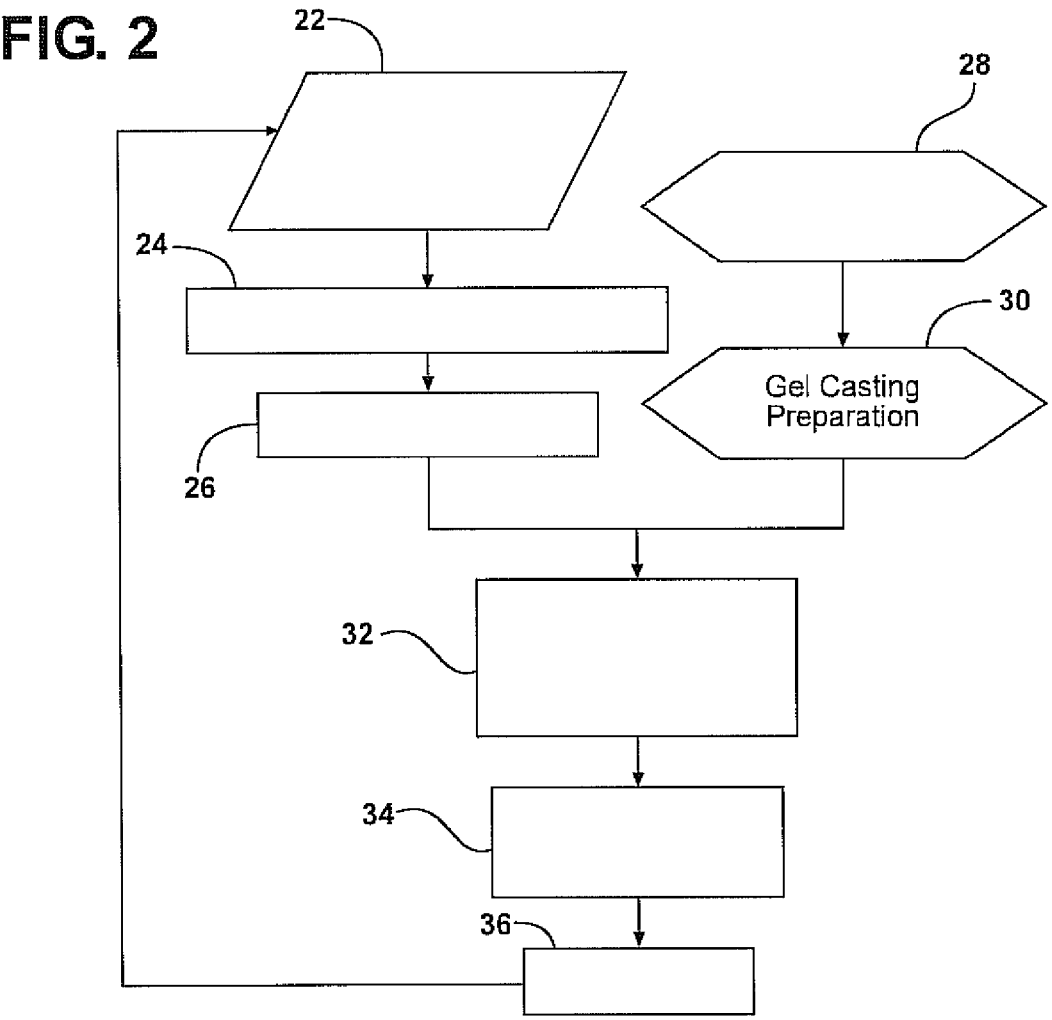
FIG. 2 is a schematic flowchart of a process for design and manufacture of an inventive component.

The design and manufacturing process of an inventive component is illustrated in the flowchart shown in FIG. 2. Initially, material strength data is collected 22 and used as a constraint in the optimization routine, which calls on finite element analysis 24 to determine the optimal dimensions of the device. Once the optimal dimensions are found, the manufacturing process proceeds as follows: a) mold fabrication 26; b) colloid preparation 28; c) gel-casting slurry preparation 30; d) mold infiltration, gel-casting, and planarization 32; and e) mold removal and sintering 34. The final parts are filtered/cleaned 36 and optionally experimentally tested in order to update material strength properties. The procedure is then repeated based on design and material property improvements through subsequent iterations. By way of example, a zirconia test bar data initially indicated 671 MPa bend strength and is consistent with the requirements for the design of miniature forceps components as shown in FIG. 1A. Subsequent generations of material are showing strength improvement with zirconia test bars at ~2400 MPa bend strength and stainless steel. Thus, additional feedback and subsequent process modification permits the design of improved surgical instruments and other components with the iterative design-manufacturing approach shown in FIG. 2.

Mold Fabrication

A polished polycrystalline alumina substrate 40 is used as substrate in this work in order to avoid the need to handle the small parts between processing steps. It is appreciated that operative substrates 40 are only limited by planarity and tolerance of the process conditions. Other operative substrates illustrative include silicon nitride, silicon carbide, glass, sapphire, YAG, nickel and alloy thereof, steel, titanium and alloys thereof, carbon, and soluble salt substrate. A substrate is chosen to preclude sintering of the inventive component thereto or any intervening layers to facilitate component lift off therefrom. A photoresist mold defining a mold cavity negative of a desired component or portion thereof is fabricated on top of the substrates using a modified UV lithography process. An exemplary photoresist operative herein for mold formation is SU8 (Microchem Corp.). It is appreciated that a positive or negative developing photoresist material is usable with a suitable mask.

Preferably, an antireflective coating 42 is spin-coated adjacent to the substrate 40 to eliminate scattered light from the reflective substrate surface to prevent curvature in the sidewalls of a mold cavity formed thereabove. An exemplary antireflective coating 42 operative herein is Barli-II 90 (Clariant Corp., Charlotte, N.C., USA). It is appreciated that any number of organic or inorganic antireflective materials are operative herein as antireflective coating 42. While organic antireflective materials tend to be applied with better coating uniformity through spin coating, inorganic material deposition often occurs with superior control over stoichiometry and thickness through gas phase deposition techniques of chemical vapor deposition (CVD), physical vapor deposition, atomic layer deposition, and enhanced versions thereof such as plasma-enhanced CVD, microwave-enhanced CVD, and the like. Exemplary of an inorganic antireflective material is dielectric silicon oxynitride. Optionally, an antireflective coating 42 is overcoating with an adhesion promoting layer 43 that promotes improved wetting by subsequent layer 44 relative to the antireflective coating 42.

Figure 3:
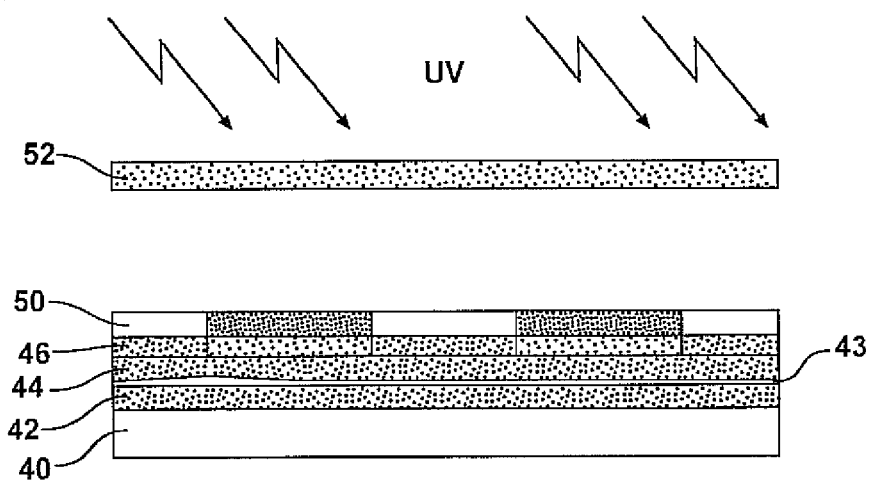
FIG. 3 is a cross-sectional view of a fabrication mold for the inventive component.

An under layer of photoresist 44 is spin-coated to form the bottom of the mold. The under layer 44 is typically between 1 and 100 µm in thickness. The under layer 44 assures part separation from the substrate or the intermediate antireflective coating 42 before sintering and acts as a bottom surface of a mold cavity. A layer 46 of photoresist is applied using spin coating. The layer 46 forms sides of a component mold cavity while the under layer 44 forms a bottom surface thereof. Optionally, a second layer of photoresist 52 on glass is used as a UV light filter during exposure. The second layer of photoresist 52 minimizes the absorption of larger wavelengths by the mask layer 50 which creates undesirable trapezoidal cross-sections in the mold and cast parts. The photoresists used in the under layer 44, layer 46, and the second photoresist layer 52 are each independently the same photoresist or vary in properties such as viscosity, development type, development conditions, and dissolution conditions. Following exposure and post exposure baking, the mold layer is developed for instance in (propyleneglycol) monomethyletheracetate (PGMEA). FIG. 3 shows the lithography layering sequence. A hard bake such as the exemplary conditions of 180° C. for 20 minutes is used to fully crosslink the photoresist after development.

Colloid Preparation

Ceramic materials are attractive components on the micron scale components due to relatively high stress to failure and the ability to be easily formed into complex shapes via powder processing into polycrystalline components. Representative ceramics operative herein illustratively include silicon carbide, boron carbide, tungsten carbide, zirconia, titania, alumina, garnet structured oxides such as metal aluminum garnets, and spinel structured materials. Additionally, a ceramic is readily reinforced with particle and fiber fillers of metallic or inorganic materials. Representative fillers include high temperature metallic whiskers or particles, such as metals of stainless steel, tungsten and titanium, carbon nanotubes, and toughening ceramic materials such as $Al_2O_3$ and/or $B_4C$. An inventive component is also readily formed from metal powders to form an inventive component with a matrix formed of materials such as aluminum, steel, tungsten, titanium, nickel and alloys thereof. It is appreciated that an inventive component formed from a metal is also amenable to inclusion modification with particle or fiber fillers. Additionally, transformation toughened ceramic exhibits mechanical properties that are desirable in structural applications. In order to obtain micron scale resolution, the final grain size of the dense ceramic must be sub-micron, therefore dictating an initial particle size in the nanometer regime of between 1 and 1000 nanometers. Additionally, nanometer sized particles facilitate complex mold filling and edge resolution of between 0.1 and 2 microns. It is appreciated that nanophase particles exhibit a size dependent melting behavior that is approximately proportioned to the inverse of the particle radius, with the most pronounced size dependency observed in the 1 to 10 nanometer size regime. This attribute is readily exploited to produce an inventive component at a reduced sintering temperature, as compared to larger precursor particles.

Well dispersed, high solids loading slurries are required to fabricate dense parts using gel-casting. By way of example, yttria partially stabilized zirconia (Tosoh Corp. TZ-3Y) is dispersed and concentrated by chemically-aided attrition milling (CAAM). During CAAM, the as-received, spray dried commercial powder is added to DI water with ammonium polyacrylate at pH 8.5 (RT Vanderbuilt, Darvan 821A) on a 1.5 wt % dry basis as the dispersant, and milled using 1 mm zirconia media. Particle diameter based on the volume distribution is reduced from 60 μm to 136 nm as measured by dynamic light scattering (Nano-S, Malvern Instruments, Southborough, Mass., USA), while electrosteric dispersion of the ceramic colloid is maintained at close particle separation distance by a high δ-potential (−49 mV, ZetaPALS, Brookhaven Instruments Corp., Holtsville, N.Y., USA). This process of dispersion is readily practiced with any of the inventive component precursor materials with routine modifications to pH, weight percent dispersant, solvent, and polymer identity.

Gel-Casting Preparation

Gel-casting of the component particulate materials provides filling of the mold cavity with component precursor particulate retained in a cured polymer matrix that precludes the shrinkage induced cracking seen in mold filling with a particulate slurry. Additionally, a gel-casting has mechanical stability to withstand processing steps between mold cavity fill and particle sintering. Gel-casting involves mixture of component precursor particulate and optional fillers in a liquid organic monomer solvent that is amenable to mold cavity fill. The monomer mixture is polymerized in situ with the aid of a catalyst to form a gelled mold fill that is stronger than a slip cast green piece formed in the same mold cavity. Representative monomers are glycerol monoacrylates selected from the group of acrylic acid, hydroxymethylacrylamide, methacrylamide, methacrylic acid, methoxy(polyethylene glycol)monomethacrylate, n-vinyl pyrrolidone, acrylamide, alkyl-acrylamides, alkyl-acrylates, alkyl-methacrylamides, alkyl-methacrylates, dimethyl aminoethyl methacrylate, dimethyl aminopropyl methacrylamide, hydroxy-alkyl acrylamides, hydroxy-alkyl methacrylamides, hydroxy-alkyl acrylates, hydroxy-alkyl methacrylates, methacrylatoethyl trimethyl ammonium chloride, methacrylamidopropryl trimethyl ammonium chloride, p-styrene sulfonic acid, and p-styrene sulfonic acid salts. Catalysts for polymerization of monomers are conventional to the art and illustratively include persulfate-amine combinations.

A specific example of gel-casting in the present invention includes methacrylamide (Sigma-Aldrich) and N,N'-methylenebisacrylamide (Sigma-Aldrich) being used as the monomers for gel-casting in a 6:1 mass ratio. The total monomer content is 5 wt.% on a dry powder basis. The monomers are dissolved into the suspension of component particulate precursor using a vortex mixer (Scientific Industries, Vortex Genie 2). A 10:1 mass ratio of ammonium peroxydisulfate (Sigma-Aldrich) and N'N',N',N'-tetramethylethylenediamine (Sigma-Aldrich) is used to initiate and catalyze the monomers, respectively. The initiator and catalyst are present at 2.5 wt % of the total monomer content.

Mold Infiltration, Gel-Casting, and Planarization

Prior to mold infiltration, the gelation reaction is initiated, leaving a working time. A working time of 5 min to 1 hour is typical but can readily be modified. The above gel-casting exemplary formulation provides a working time of approximately 25 min. The gelation reaction forms a network of cross-linked polymer between particles which provides additional green strength during the drying and mold removal steps. Following initiation, slurry is cast into the molds via a screen printing squeegee. A typical casting rate is 10 centimeters per second. Multiple passes with the squeegee are preferred to ensure complete mold filling with no entrapped air pockets, with the final squeegee pass preferably leaving a thin (1 mm) layer of excess slurry on top of the mold cavity. Gelation is preferably carried out under conditions to minimize drying and allow the reaction to be carried to completion. Representative conditions include a 100% relative humidity $N_2$ environment. Following gelation, the samples are allowed to dry, for example in ambient atmosphere. The excess slurry on top of the mold is removed until the mold surface becomes visible. An ethanol wipe is well suited to remove excess slurry. Dishing out of slurry from within the mold cavity is minimized to less than 5 μm. A cross-sectional view of a completed mold is illustrated in FIG. 4.

Mold Removal and Sintering

While mold removal is readily achieved through solvent removal with organic solvents, such developer or base such as KOH or pyrolysis, reactive ion etching (RIE) is preferably used to remove the entire mold without inducing the dimensional changes that are typically seen with pyrolysis or damage to the green ware filling the mold cavity. Representative RIE system parameters are set to 50 sccm $O_2$, 6 sccm $SF_6$, 350 W power, and an etch time of 75 minutes. Substrates are placed into a standard box furnace and sintered at 1° C./min to 300° C. with a 1 hr hold, 1° C./min to 450° C., 1° C./min to 600° C. with no hold, and 10° C./min to 1300° C. for 2 hrs with a furnace cool. Sintered components can be individually manipulated for further characterization or testing using a micromanipulator. FIG. 5 shows an exemplary fabricated zirconia test bar according to the present invention. It is appreciated that a sintered component exhibits a degree of shrinkage relative to the dimensions of the mold cavity. The shrinkage between a green ware mold fill and a sintered and densified material flows known ceramic densification principles and depends on factors including amount of gel polymer present, precursor particulate size, precursor particulate size distribution, and thermal time-temperature sintering profile.

This inventive manufacturing process is advantageous because components are fabricated with higher aspect ratios than previously available sharp edges (~1 micron) while retaining a resolution of 2 microns in a mass production regime.

Still more complex three-dimensional articles are readily formed by lamination prior to RIE and densification. Lamination involves two dissimilar green components being brought into contact to allow sintering to form a composite component additive of the two mold cavity shapes in a given orientation along the overlapping interface between the components. In this way still more complex shapes are formed or an aspect ratio of $L:H_{min}:T_{min}$ of 20-80:1:05-10 is achieved from separate elements that each do not satisfy this aspect ratio requirement. The sintering of two green ware mold fills after RIE is particularly well suited for the formation of lap joints between the green ware.

Micro Forceps Produced from Sintered Components

Figure 6A:
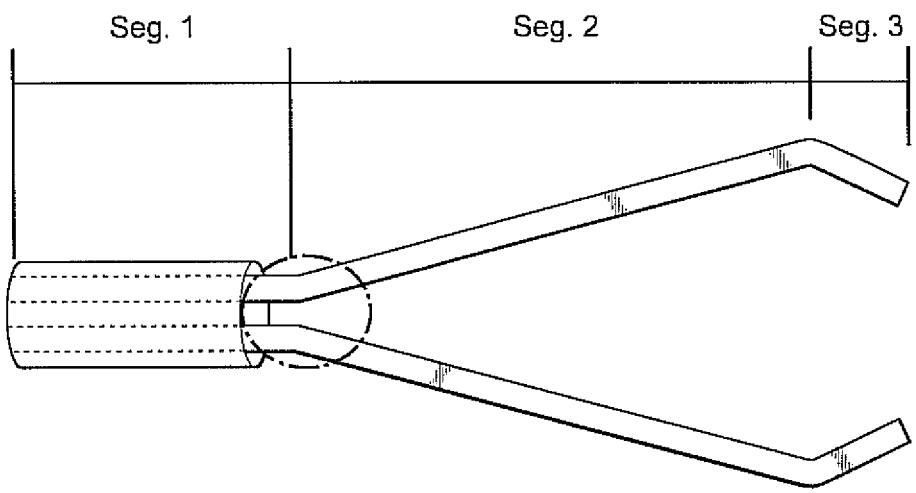
FIGS. 6A and 6B are a schematic of a component of FIG. 1A as part of a pair of micro forceps in open (A) and closed (B) configurations.
Figure 6B:
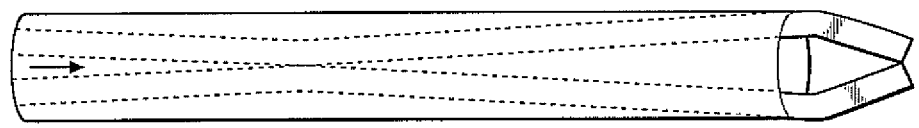

An inventive component as part of a pair of micro forceps is a monolithic compliant mechanism that uses large elastic deformation to achieve motion. Since compliant mechanisms can be monolithic they are ideal for small-scale applications because manufacturing and assembling of tiny parts are avoided. In addition, considering the nanoparticulate manufacturing process is currently limited to 2D parts, a compliant micro forceps is a good candidate for fabrication. The micro forceps consists of two parts, an upper and lower arm. FIG. 6 illustrates the basic geometry and actuation principle of the device based on the component shown in FIG. 1A.

The micro forceps is designed to fit inside the inner diameter (ID) of the outer sheath (shown in ghost) used for actuation. Here, tool dimensions should not require an outer sheath larger than 1 mm ID. As shown above, an outer sheath (made of medical grade stainless steel or other biocompatible material) encloses segment 1 of the device. As the sheath is advanced forward, the forceps arms are forced to displace toward one another, thus producing a grasping motion. The device is intended to grasp tissue, such as the gastric wall during NOTES procedures. The two component arms are separated and come into contact with one another as the sheath is advanced forward. This design feature results in stress relief as contact occurs between the forceps arms at point A.

Figures 8A, 8B:
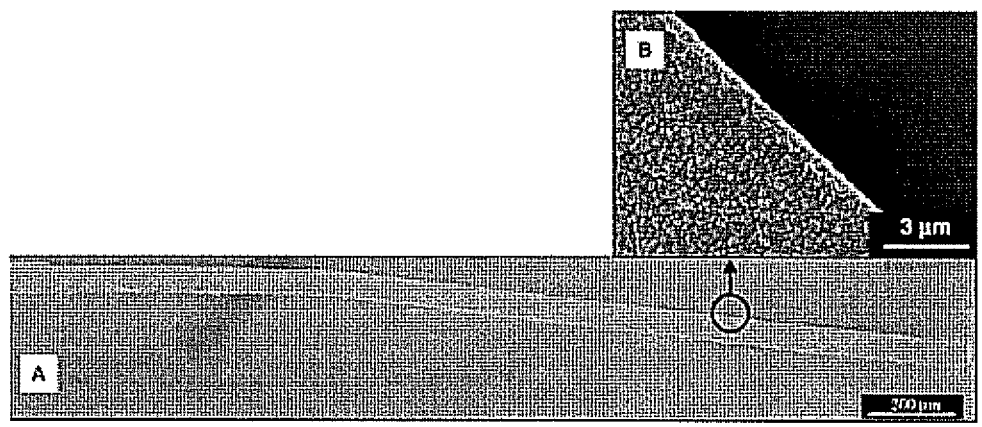
FIGS. 8A and 8B are an SEM of an inventive component of FIG. 7 and a magnified SEM of edge resolution from FIG. 8A (B), teeth on the segment 3 are noted.

Due to symmetry, one-half of the device is modeled as a cantilever beam undergoing large deformation. Geometric variables can be seen in FIG. 7, where L and $L_1$, $L_2$, and $L_3$ are defined with respect to FIG. 1A. Other variables are w=width (synonymous with T with respect to FIG. 1A), $\delta_{hop}$=half opening, $\delta_{hs}$=half separation distance and $H_3$=Height of segment 3. SEM images of such a component is shown in FIGS. 8A and 8B.

The distal tips of the micro forceps come into contact first when the device is closed, followed by the jaw surfaces (segment 3) gradually becoming parallel with additional pressure. Therefore, segment three is directed inward with dimensions $L_3$ and $H_3$ set to 0.075 mm and 0.05 mm, respectively. To simplify the number of geometric variables, $L_1$ is set to 30% of the total length (L) and $\delta_{hs}$ is set to 0.015 mm. The thickness of the device into the page, T, is directly related to the thickness of the photoresist used as a mold. For this example, a 100 μm photoresist thickness is used for manufacturing. The final thickness is scaled by a thickness shrinkage factor due to the sintering process.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A polycrystalline mesoscale component having an overall length L divided into at least a first segment and a second segment, the second segment extending from the first segment at a nonlinear angle, the first segment having a first segment height $H_1$, and a first segment thickness $T_1$, the second segment having a second segment height $H_2$ and a second segment thickness $T_2$, the lesser of $H_1$ and $H_2$ defining a minimum segment height $H_{min}$ and the lesser of $T_1$ and $T_2$ defining a minimum segment thickness $T_{min}$, the component having a ratio of $L:H_{min}:T_{min}$ of 20-80:1:0.5-10 where the $H_{min}$ is between 5 and 500 microns.

2. The component of claim 1 wherein the ratio is greater than 40:1:0.5-3.

3. The component of claim 1 wherein the angle is acute.

4. The component of claim 1 wherein the first segment and the second segment are rectilinear in cross section.

5. The component of claim 1 wherein a planar surface area of the overall length and height of the component is less than 40% of the overall length times the overall height.

6. A polycrystalline mesoscale component having an overall length L divided into at least a first segment and a second segment, the second segment extending from the first segment at a nonlinear angle, the first segment having a first segment height $H_1$, and a first segment thickness $T_1$, the second segment having a second segment height $H_2$ and a second segment thickness $T_2$, the lesser of $H_1$ and $H_2$ defining a minimum segment height $H_{min}$ and the lesser of $T_1$ and $T_2$ defining a minimum segment thickness $T_{min}$, the component having a ratio of $L:H_{min}:T_{min}$ of 20-80:1:0.5-10 where the $H_{min}$ is between 5 and 500 microns wherein a surface defining the first segment thickness has an edge resolution of between 0.1 and 2 microns.

7. The component of claim 6 wherein the edge resolution is less than 1 micron.

8. A polycrystalline mesoscale component having an overall length L divided into at least a first segment and a second segment, the second segment extending from the first segment at a nonlinear angle, the first segment having a first segment height $H_1$, and a first segment thickness $T_1$, the second segment having a second segment height $H_2$ and a second segment thickness $T_2$, the lesser of $H_1$ and $H_2$ defining a minimum segment height $H_{min}$ and the lesser of $T_1$ and $T_2$ defining a minimum segment thickness $T_{min}$, the component having a ratio of $L:H_{min}:T_{min}$ of 20-80:1:0.5-10 where the $H_{min}$ is between 5 and 500 microns wherein the component has an average sintered grain size of between 50 nanometers and 10 microns and formed of a ceramic.

9. The component of claim 8 wherein a surface defining the first segment thickness has an edge resolution of between 0.1 and 2 microns.

10. The component of claim 9 wherein the edge resolution is less than 1 micron.

11. A polycrystalline mesoscale component having an overall length L divided into at least a first segment and a second segment, the second segment extending from the first segment at a nonlinear angle, the first segment having a first segment height $H_1$, and a first segment thickness $T_1$, the second segment having a second segment height $H_2$ and a second segment thickness $T_2$, the lesser of $H_1$ and $H_2$ defining a minimum segment height $H_{min}$ and the lesser of $T_1$ and $T_2$ defining a minimum segment thickness $T_{min}$, the component having a ratio of $L:H_{min}:T_{min}$ of 20-80:1:0.5-10 where the $H_{min}$ is between 5 and 500 microns wherein the component has an average sintered grain size of between 100 nanometers and 100 microns and formed of a metal.

12. The component of claim 11 wherein a surface defining the first segment thickness has an edge resolution of between 0.1 and 2 microns.

13. The component of claim 12 wherein the edge resolution is less than 1 micron.

14. A polycrystalline mesoscale component formed from a ceramic having an overall length L divided into at least a first segment and a second segment, the second segment extending from the first segment at a nonlinear angle, the first segment having a first segment height $H_1$, and a first segment thickness $T_1$, the second segment having a second segment height $H_2$ and a second segment thickness $T_2$, the lesser of $H_1$ and $H_2$ defining a minimum segment height $H_{min}$ and the lesser of $T_1$ and $T_2$ defining a minimum segment thickness $T_{min}$, the component having a ratio of $L:H_{min}:T_{min}$ of 20-80:1:0.5-10 where the $H_{min}$ is between 5 and 500 microns.

15. The component of claim 14 wherein a surface defining the first segment thickness has an edge resolution of between 0.1 and 2 microns.

16. The component of claim 15 wherein the edge resolution is less than 1 micron.

17. A polycrystalline mesoscale component formed from a metal having an overall length L divided into at least a first segment and a second segment, the second segment extending from the first segment at a nonlinear angle, the first segment having a first segment height $H_1$, and a first segment thickness $T_1$, the second segment having a second segment height $H_2$ and a second segment thickness $T_2$, the lesser of $H_1$ and $H_2$ defining a minimum segment height $H_{min}$ and the lesser of $T_1$ and $T_2$ defining a minimum segment thickness $T_{min}$, the component having a ratio of $L:H_{min}:T_{min}$ of 20-80:1:0.5-10 where the $H_{min}$ is between 5 and 500 microns.

18. The component of claim 17 wherein a surface defining the first segment thickness has an edge resolution of between 0.1 and 2 microns.

19. The component of claim 18 wherein the edge resolution is less than 1 micron.

\* \* \* \* \*